(12) United States Patent
Kim et al.

(10) Patent No.: US 7,731,994 B2
(45) Date of Patent: Jun. 8, 2010

(54) PHARMACEUTICAL COMPOSITION FOR PROTECTING NEURONS COMPRISING EXTRACT OF LITHOSPERMUM ERYTHROTHIZON SIEB. ET. ZUCC OR ACETYLSHIKONIN ISOLATED THEREFROM AS AN EFFECTIVE INGREDIENT

(75) Inventors: Ho Cheol Kim, Seoul (KR); Ha Young Lee, Kyounggi-do (KR); Ni Na Ha, Incheon (KR); Min Jung Kong, Kyounggi-do (KR); Seung Ju Roh, Daejeon (KR); Nak Sul Seong, Kyounggi-do (KR); Geum Soog Kim, Kyounggi-do (KR); Yun Tai Kim, Incheon (KR); Youngmin Bu, Seoul (KR)

(73) Assignee: Industry Academic Cooperation Foundation of Kyunghee University, Seoul (KR)

(*) Notice: Subject to any disclaimer, the term of this patent is extended or adjusted under 35 U.S.C. 154(b) by 245 days.

(21) Appl. No.: 11/762,350

(22) Filed: Jun. 13, 2007

(65) Prior Publication Data

US 2008/0311228 A1 Dec. 18, 2008

(51) Int. Cl.
*A61K 36/00* (2006.01)
(52) U.S. Cl. .................................................. 424/725
(58) Field of Classification Search .................. None
See application file for complete search history.

(56) References Cited

U.S. PATENT DOCUMENTS 5,589,154 A * 12/1996 Anderson .................. 424/1.41

FOREIGN PATENT DOCUMENTS

| KR | 2006064068 A | * | 6/2006 |
| KR | 10-2004-0102090 | | 10/2006 |

OTHER PUBLICATIONS

Vickers, J. C.; A Vaccine Aginst Alzheimer's Disease; Drugs Aging (2002), 19 (7) pp. 487-494.*
Kermer et al. Neuronal Apoptosis in Neurodegenerative Diseases; From Basic Research to Clinical Application; Neurodegenerative Diseases, 2004,(1) pp. 9-19.*

* cited by examiner

*Primary Examiner*—Patricia Leith
(74) *Attorney, Agent, or Firm*—Lucas & Mercanti, LLP

(57) ABSTRACT

The present invention relates to a pharmaceutical composition for protecting neurons or for preventing and treating ischemic neuronal diseases comprising the extract of *Lithospermum erythrorhizon* Sieb. Et Zucc extracted with water, low-alcohols or their mixture or acetylshikonin separated therefrom as an effective ingredient. The extract of *Lithospermum erythrorhizon* Sieb. Et. Zucc or acetylshikonin separated therefrom of the present invention has neuronal protective effect, so that it not only interrupts the development of ischemic neuronal diseases but also is very safe, indicating that the extract or acetylshikonin can be used as a medicinal drug for prevention and treatment of degenerative brain disease caused by neuronal apoptosis such as stroke, apoplexy, dementia, Alzheimer's disease, Parkinson's disease, Huntington's disease, Pick's disease and Creutzfeldt-Jakob disease and further can be developed as functional health food.

5 Claims, 5 Drawing Sheets

PHARMACEUTICAL COMPOSITION FOR PROTECTING NEURONS COMPRISING EXTRACT OF LITHOSPERMUM ERYTHROTHIZON SIEB. ET. ZUCC OR ACETYLSHIKONIN ISOLATED THEREFROM AS AN EFFECTIVE INGREDIENT

BACKGROUND OF THE INVENTION (a) Field of the Invention

The present invention relates to a pharmaceutical composition for protecting neurons or for preventing and treating ischemic neuronal diseases, more precisely a pharmaceutical composition for protecting neurons or for preventing and treating ischemic neuronal diseases comprising a plant extract or a single compound extracted therefrom which is effectively used for the treatment of degenerative brain diseases caused by neuronal apoptosis as an effective ingredient and functional health food comprising the same.

(b) Description of the Related Art

Nerve system is largely composed of neurons and neuroglia cells, and the neuroglia cells take 90% of the total brain cells in number and take 50% of the total brain in volume. The neuroglia cells in central nervous system are composed of astrocytes, oligodendrocytes and microglia. And microglia cells are inflammatory cells that take 5-10% of the total brain cells and have been confirmed to be macrophage like immuno-functional cells which are activated when brain damage, including degenerative brain disease and stroke, occurs by some reasons even though their role in brain under normal conditions has not been disclosed yet (Minghetti L, et al., *Prog. Neurobio. I.* 54(1), pp 99-125, 1998). Unlike normal cells, the activated microglia cells exhibit active phagocytosis and vigorous proliferation, so that they induce expressions of various genes such as cytokine, inducible nitric oxide synthase (iNOS) and cyclooxygenase-s (COX-2), suggesting that they generate various inflammation mediators (Dawson V L, et al., *J. Neurosci.*, 13, pp 2651-2661, 1993). There have been so many proofs reported saying that such inflammation mediators generated as the above are one of the reasons that cause degenerative brain diseases such as Alzheimer's disease, Parkinson's disease, stroke and dementia (wood P L, et al., *Neurol. Res.*, 17, pp 242-248, 1995).

The inflammation mediators generated by the activated microglia cells produce nitric oxide (NO) (Feldman P L, et al., *Chem Eng. News.*, 12, pp 26-38, 1993). Nitric oxide is generated by nitric oxide synthase (NOS) and this enzyme can be classified into constitutive NOS (cHOS) that produces nitric oxide for normal physiological functions including neurotransmission, blood clotting and blood pressure control; and inducible nitric oxide that is specifically induced under special circumstances. Generation of constitutive NOS (cNOS) depends on calcium ($Ca^{2+}$) and calmodulin (CaM) and only small amount of cNOS can be generated within a short period of time by a certain stimulus. On the other hand, the generation of inducible NOS (iNOS) is quite independent and iNOS is not activated under the normal conditions but once its expression is induced by the stimulus of lipopolysaccharides, iNOS can be mass-produced for a certain period of time and thus iNOS produces inflammatory cytokines such as interferon-gamma (INF-gamma), interleukin-1beta, cancer necrosis factor-alpha, etc. (Mayer B., et al., *FEBS Lett*, 288, pp187-191, 1991). Excessive nitric oxide generated by inducible NOS and inflammatory cytokine generated aftermath lower blood pressure significantly by extending blood vessels in sepsis patients, make inflammation worse by accelerating biosynthesis of inflammation mediators such as prostaglandins by activating COX-2, and is deeply involved in the development and progress of brain diseases resulted from neuronal apoptosis and aggravated inflammation.

It has been an urgent request therefore to develop a safe novel neuroprotective agent with fewer side effects that can inhibit significantly the expressions of inflammatory cytokines causing brain disease and making inflammation worse. And it is also requested to establish a specialized medicine market for neuroprotective agents.

Acetylshikonin used in this invention is a naphtoquinone compound extracted and isolated from *Lithospermum erythrorhizon* Sieb. Et Zucc, an oriental herb medicine which has long been used for the treatment of dermatitis in Korea and China.

*Lithospermum erythrorhizon* Sieb. Et Zucc (gromwell) is a perennial plant. Its root contains acetylshikonin, shikonin, alkannan, isobutyrylshikonin, beta/beta-dimethylacrylshikonin, beta-hydroxyisovalerylshikonin, and teracryishikonin, and the purple color of the root is attributed to acetylshikonin. Shikonin or acetylshikonin has functions of inhibiting edema, promoting granulation growth and accelerating wound healing, in particular boosting regeneration of destroyed or damaged cells by burn or ulcer. These compounds also have antimicrobial activity against bacteria or virus and exhibit a strong capillary permeability. In addition, these compounds have been known to have functions of improving blood circulation and reducing blood sugar and anticancer activity as well (Jung B S and Shin M K, Hyangyak daesajeon, 1998, pp 891-892). However, there has been no reports in association with the therapeutic effect of the extract of *Lithospermum erythrorhizon* Sieb. Et Zucc or acetylshikonin on brain disease by inhibiting inflammatory cytokine and preventing neuronal apoptosis.

Therefore, the present inventors investigated in this invention the effect of the extract of *Lithospermum erythrorhizon* Sieb. Et Zucc and acetylshikonin separated therefrom on inflammatory cytokine by various biochemical experiments, examined the possibility of interruption of nitric oxide and inflammatory cytokine by molecular biological approaches and further investigated the mechanism of the extract of *Lithospermum erythrorhizon* Sieb. Et Zucc and acetylshikonin for protecting neurons particularly from ischemic neuronal apoptosis by using animal models with local brain ischemia.

As a result, the extract of *Lithospermum erythrorhizon* Sieb. Et Zucc of the present invention extracted by water, low-alcohol or their mixed solution and acetylshikonin separated and isolated from the extract inhibited expressions of various inflammatory cytokines including inducible nitric oxide synthase in vitro, and thereby the inventors confirmed the mechanism of the extract and acetylshikonin to interrupt over-production of nitric oxide and to protect neurons from apoptosis caused by brain ischemia by using rats with local brain ischemia induced by middle cerebral arterial occlusion. In conclusion, the present inventors completed this invention by confirming that acetylshikonin has an activity of protecting neurons and a function of inhibiting neuronal apoptosis by investigating the therapeutic effect and therapeutic mechanism of acetylshikonin for ischemic brain diseases.

SUMMARY OF THE INVENTION

The present invention provides a pharmaceutical composition for prevention and treatment of degenerative brain disease comprising the extract of *Lithospermum erythrorhizon* Sieb. Et Zucc extracted by water, alcohol or a mixture thereof as an effective ingredient.

The present invention also provides a pharmaceutical composition for prevention and treatment of degenerative brain disease comprising acetylshikonin represented by the following formula 1 as an effective ingredient.

<Formula 1>

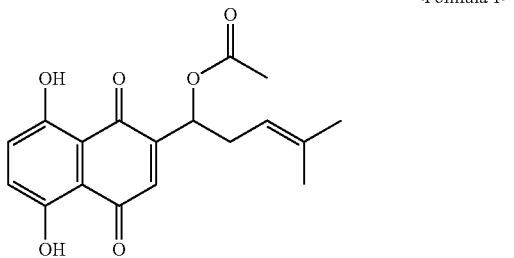

Degenerative brain disease herein is characteristically induced by neuronal apoptosis, which is exemplified by stroke, apoplexy, dementia, Alzheimer's disease, Parkinson's disease, Huntington's disease, Pick's disease and Creutzfeldt-Jakob disease.

The present invention further provides functional health food for prevention of degenerative brain disease comprising the extract of Lithospermum erythrorhizon Sieb. Et Zucc and/or acetylshikonin as an effective ingredient.

The present invention also provides a method for protecting neurons containing the step of administering an effective dosage of the extract of Lithospermum erythrorhizon Sieb. Et Zucc or acetylshikonin to inhibit neuronal apoptosis.

The present invention also provides a preventive and treatment method for degenerative brain disease caused by neuronal apoptosis comprising the step of administering the effective dose of the extract of Lithospermum erythrorhizon Sieb. Et Zucc or acetylshikonin to inhibit neuronal apoptosis.

DETAILED DESCRIPTION OF THE PREFERRED EMBODIMENTS

Figure 1:
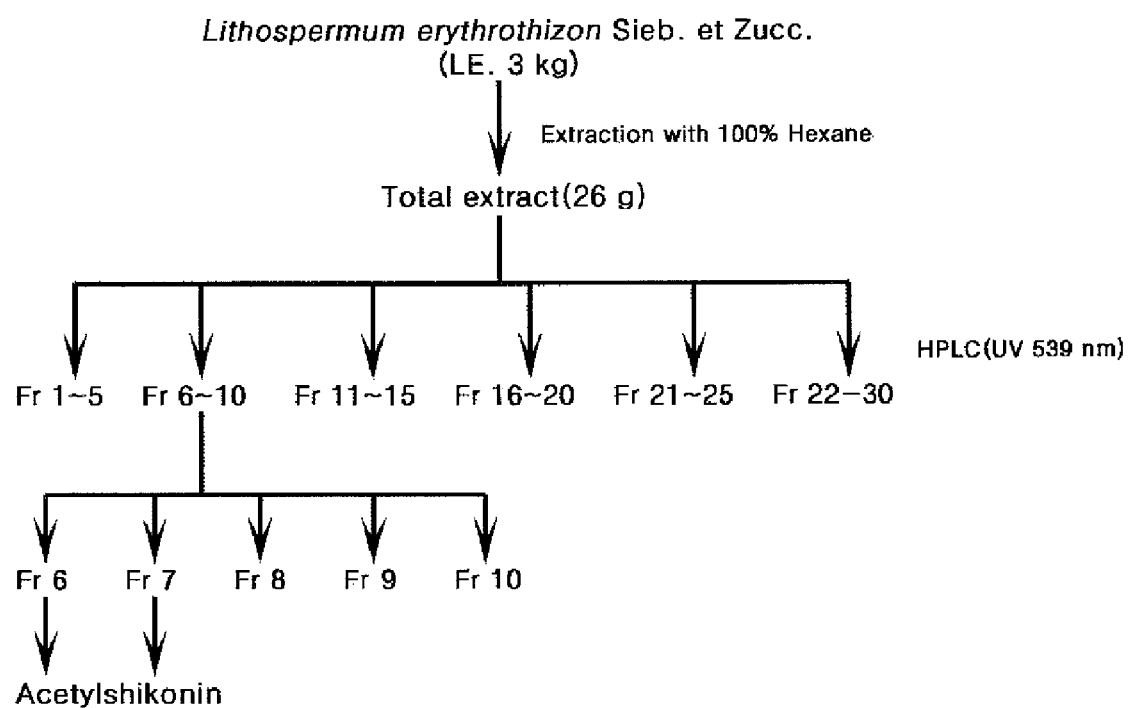
FIG. 1 is a diagram illustrating the separation and purification of acetylshikonin from Lithospermum erythrorhizon Sieb. Et Zucc.

Hereinafter, the present invention is described in detail.

The present inventors prepared the water extract, ethanol extract, 70% ethanol extract and hexane extract from the root of Lithospermum erythrorhizon Sieb. Et Zucc. Among these extracts, hexane extract proceeded onto column chromatography to separate acetylshikonin (see FIG. 1). The present inventors investigated the inhibition of neuronal apoptosis by the extract of Lithospermum erythrorhizon Sieb. Et Zucc or acetylshikonin in stroke animal models. As a result, damaged brain tissues were protected 44.73% by the water extract of Lithospermum erythrorhizon Sieb. Et Zucc, 60.72% by the ethanol extract and 52.63% by 70% ethanol extract, compared with the control (see FIG. 2). The administration of 1 mg/kg of acetylshikonin resulted in the protective effect on the damaged brain tissues approximately up to 46.88% and the administration of 3 mg/kg of acetylshikonin brought 68.75% brain tissue protective effect, suggesting that the protection of damaged brain tissues increased dose-dependently (see FIG. 3). Then, the present inventors investigated the effect of acetylshikonin on the generation of nitric oxide in microglia and BV-2 cells activated by LPS. As a result, acetylshikonin inhibited the generation of nitric oxide dose dependently at the levels of gene and protein (see FIGS. 4a, 4b, 5a and 5b). The above results indicate that acetylshikonin inhibits the expression of nitric oxide synthase so that inhibit the generation of nitric oxide, and thereby acetylshikonin has a protective effect on brain tissue damage.

The present invention provides a pharmaceutical composition for prevention and treatment of degenerative brain disease comprising the extract of Lithospermum erythrorhizon Sieb. Et Zucc extracted by water, alcohol or a mixture thereof as an effective ingredient.

Alcohol herein is preferably low-alcohol, and C1-C3 alcohol is more preferred. For the mixture of water and alcohol, 10~90% ethanol is preferred and 70% ethanol is more preferred but not always limited thereto. The preferable amount of extraction solvent for preparing the extract of Lithospermum erythrorhizon Sieb. Et Zucc is approximately 1-10 times the weight of Lithospermum erythrorhizon Sieb. Et Zucc and 5 times the weight is more preferred but not always limited thereto. Extraction time is preferably 1-24 hours and 1-12 hours are more preferred and 5 hours are most preferred, but not always limited thereto. Preferable extraction methods are enfleurage, hot water extraction, ultrasonic extraction, reflux extraction and immersion extraction, and reflux extraction is more preferred but not always limited thereto. Extraction temperature is preferably 10~100° C. and 80° C. is more preferred, but not always limited thereto. The roots, stems and leaves of Lithospermum erythrorhizon Sieb. Et Zucc are all used and the roots are more preferred but not always limited thereto.

The present inventors prepared the extract of Lithospermum erythrorhizon Sieb. Et Zucc from the roots by using water, ethanol and 70% ethanol. Then the inventors further investigated the defensive effect of the water extract, ethanol extract and 70% ethanol extract of Lithospermum erythrorhizon Sieb. Et Zucc in rats with local brain ischemia induced by middle cerebral arterial occlusion. As a result, the protective effect on the damage of brain tissues was respectively 44.73% by the water extract, 60.72% by the ethanol extract and 52.63% by the 70% ethanol extract, compared with the control (see FIG. 2). Therefore, the extract of Lithos-

*permum erythrorhizon* Sieb. Et Zucc of the present invention can be effectively used for prevention and treatment of degenerative brain disease.

Degenerative brain disease herein is characteristically induced by neuronal apoptosis, which is exemplified by stroke, apoplexy, dementia, Alzheimer's disease, Parkinson's disease, Huntington's disease, Pick's disease and Creutzfeldt-Jakob disease.

The present invention also provides a pharmaceutical composition for prevention and treatment of degenerative brain disease comprising acetylshikonin represented by the following formula 1 as an effective ingredient.

<Formula 1>

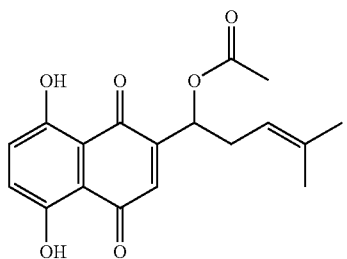

Acetylshikonin of the invention is characteristically isolated from the fractions obtained by adding a fat-soluble solvent to the water extract, ethanol extract or 70% ethanol extract of *Lithospermum erythrorhizon* Sieb. Et Zucc or directly from the extract of *Lithospermum erythrorhizon* Sieb. Et Zucc extracted using a fat-soluble solvent.

The fat-soluble solvent herein is preferably one of non-polar solvents such as n-butane, hexane, ethylacetate and chloroform, and hexane is more preferred, but not always limited thereto.

The extraction of acetylshikonin is performed as follows; a non-polar solvent such as hexane, ethylacetate and chloroform is added by the volume of approximately 1-10 times the weight of Lithospermum erythrorhizon Sieb. Et Zucc root powder, more preferably 1-5 times the weight, followed by one of extraction methods including enfleurage, hot water extraction, ultrasonic extraction and reflux extraction, at room temperature for 7-20 days, more preferably 7-10 days. In the present invention, extraction was performed by reflux extraction several times and the extract was vacuum-concentrated at 20~100° C., more preferably 30-70° C., to give a non-polar solvent-soluble extract. The obtained non-polar-soluble extract proceeded onto silica gel column chromatography. At this time, the mixed solvent of hexane and ethylacetate (Hexane:EtOAc=30:1→→1:11) and the mixed solvent of ethylacetate and methanol (EtOAc:MeOH=25:1→→1:2) were used as an extraction solvent system with increasing polarity. The extraction was repeated several times to separate and purify acetylshikonin of the present invention.

It was confirmed by in vitro experiment that the extract of *Lithospermum erythrorhizon* Sieb. Et Zucc prepared by the method of the invention and/or acetylshikonin separated therefrom has preventive and therapeutic effect on neuronal damage caused by brain ischemia by protecting neuronal apoptosis in animal models with local brain ischemia induced by middle cerebral arterial occlusion (see FIG. 3).

Therefore, the present invention provides a pharmaceutical composition for prevention and treatment for degenerative brain disease comprising the extract of *Lithospermum erythrorhizon* Sieb. Et Zucc of the invention or acetylshikonin separated therefrom as an effective ingredient.

The extract of *Lithospermum erythrorhizon* Sieb. Et Zucc and/or acetylshikonin are medicinal materials that have been long used as a herb medicine and thus the extracts of the invention are safe without toxicity or side effects.

The pharmaceutical composition of the invention for prevention and treatment of degenerative brain disease contains the extract of Lithospermum erythrorhizon Sieb. Et Zucc and/or acetylshikonin as an effective ingredient at the concentration of 0.001-50 weight % for the total weight of the composition.

The pharmaceutical composition of the invention containing the extract of *Lithospermum erythrorhizon* Sieb. Et Zucc and/or acetylshikonin can additionally contain pharmaceutically acceptable carriers, excipients and diluents.

For the administration, the pharmaceutical composition of the invention can be prepared as the form of pharmaceutically acceptable salt or prepared as a single compound or mixed with other pharmaceutically active compounds.

The pharmaceutical composition of the invention can be administered orally or parenterally and be used in general forms of pharmaceutical formulation. Formulations for oral administration are powders, granules, pills, capsules, suspensions, emulsions, syrups, aerosols, etc. Formulations for parenteral administration are external preparations, suppositories and sterilized injections. The composition containing acetylshikonin can contains lactose, dextrose, sucrose, sorbitol, mannitol, xilytole, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate and mineral oil. The composition of the invention can be prepared by mixing with generally used fillers, extenders, binders, wetting agents, disintegrating agents, diluents such as surfactant, or excipients. Solid formulations for oral administration are tablets, pills, dusting powders, granules and capsules. These solid formulations are prepared by mixing one or more suitable excipients such as starch, calcium carbonate, sucrose, lactose, gelatin, etc. Except for the simple excipients, lubricants, for example magnesium stearate, talc, etc, can be used. Liquid formulations for oral administration are suspensions, solutions, emulsions and syrups, and the abovementioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The effective dosage of the extract and/or acetylshikonin of the present invention varies from the formulation, administration pathway, age, weight, gender, severity of a disease, diet, administration frequency and pathway, excretion and sensitivity. In general, the dosage can be determined by the people in this field with consideration of the goal of the treatment or preventive effect. The dosage is 0.0001~100 mg/kg per day, and preferably 0.001~100 mg/kg per day. Administration frequency is once a day or preferably a few times a day. However, this dosage cannot limit the scope of the present invention in any aspects.

The compound of the present invention can be administered to mammalians including mouse, rat, cattle, and human through various administration pathways, which can be expected as oral administration, endorectal, intravenous, intramuscular, hypodermic, endometrial or intracerebroventricular injection.

The present invention also provides functional health food for prevention of degenerative brain disease comprising the extract of *Lithospermum erythrorhizon* Sieb. Et Zucc and/or acetylshikonin as an effective ingredient.

The extract of *Lithospermum erythrorhizon* Sieb. Et Zucc and/or acetylshikonin of the invention is addable to such food as beveragqs, gums, tea, vitamin complex, and other functional foods. The composition of the present invention can be included in food or beverages for the purpose of preventing and improving degenerative brain disease. At this time, the content of the extract of *Lithospermum erythrorhizon* Sieb. Et Zucc and/or acetylshikonin in food is generally 0.01~15 weight % for the total weight of food, and the content of the extract of *Lithospermum erythrorhizon* Sieb. Et Zucc and/or acetylshikonin in beverage is 0.02~5 g/100 ml and more preferably 0.3~1 g/100 ml.

The functional health food of the present invention can be prepared as tablets, capsules, pills, liquid, etc.

Functional health food containing the extract of *Lithospermum erythrorhizon* Sieb. Et Zucc and/or acetylshikonin of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. As a sweetener, either natural sweetener such as thaumatin and stevia extract (rebaudioside A and glycyrrhizin) or artificial sweetener such as saccharin and aspartame can be used. The ratio of natural carbohydrate to the functional health food of the present invention is preferably 1~20 g to 100 ml, more preferably 5~12 g to 100 ml.

In addition to the ingredients mentioned above, the functional health food of the present invention can include in variety of nutrients, vitamins, minerals (electrolytes), synthetic flavors, natural flavors, coloring agents, pectic acid and its salts, arginic acid and its salts, organic acid, protective colloidal viscosifiers, pH regulators, stabilizers, antiseptics, glycerin, alcohols, carbonators which used to be added to soda, etc. The functional health food of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0.001~20 weight part per 100 weight part of the functional health food of the invention.

The present invention also provides a method for protecting neurons containing the step of administering an effective dosage of the extract of *Lithospermum erythrorhizon* Sieb. Et Zucc and/or acetylshikonin to inhibit neuronal apoptosis.

At this time, the effective dose of the extract of *Lithospermum erythrorhizon* Sieb. Et Zucc to inhibit neuronal apoptosis is 0.001-100 mg/kg/day and more preferably 0.5-10 ug/kg/day, and the effective dose of acetylshikonin is 0.0001-100 ug/kg/day and more preferably 0.001-10 mg/kg/day.

The present invention also provides a preventive and treatment method for degenerative brain disease caused by neuronal apoptosis comprising the step of administering the effective dose of the extract of *Lithospermum erythrorhizon* Sieb. Et Zucc and/or acetylshikonin to inhibit neuronal apoptosis.

At this time, the effective dose of the extract of *Lithospermum erythrorhizon* Sieb. Et Zucc to inhibit neuronal apoptosis is 0.001-100 mg/kg/day and more preferably 0.5-10 ug/kg/day, and the effective dose of acetylshikonin is 0.0001-100 ug/kg/day and more preferably 0.001-10 mg/kg/day.

Degenerative brain disease herein is characteristically induced by neuronal apoptosis, which is exemplified by stroke, apoplexy, dementia, Alzheimer's disease, Parkinson's disease, Huntington's disease, Pick's disease and Creutzfeldt-Jakob disease.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of the Extract of *Lithospermum erythrorhizon* Sieb. Et Zucc

<1-1> Preparation of Water Extract

Roots of *Lithospermum erythrorhizon* Sieb. Et Zucc grown in Korea were purchased from outlet store of Korea Medicine Herbal Association, Jekidong, Seoul in 2003, which were then verified by Department of Herbal Pharmacology, Graduate School of East-West Medical Science, Kyung Hee University. The root samples were dried and pulverized. 3 kg of the root powder was added into 20 L of water, followed by reflux extraction at 100° C. for 3 hours. The mixture stood for 5 hours to obtain supernatant. The supernatant was filtered and vacuum concentrated to give 340 g of water extract.

<1-2> Preparation of Ethanol Extraction

Roots of *Lithospermum erythrorhizon* Sieb. Et Zucc grown in Korea were purchased from outlet store of Korea Medicine Herbal Association, Jekidong, Seoul in 2003, which were then verified by Department of Herbal Pharmacology, Graduate School of East-West Medical Science, Kyung Hee University. The root samples were dried and pulverized. 3 kg of the root powder was added into 20 L of ethanol, followed by reflux-extraction for 5 hours. The mixture stood for 3 hours to obtain supernatant. The supernatant was filtered and vacuum concentrated to give 275 g of ethanol extract.

<1-3> Preparation of 70% Ethanol Extract

Roots of *Lithospermum erythrorhizon* Sieb. Et Zucc grown in Korea were purchased from outlet store of Korea Medicine Herbal Association, Jekidong, Seoul in 2003, which were then verified by Department of Herbal Pharmacology, Graduate School of East-West Medical Science, Kyung Hee University. The root samples were dried and pulverized. 3 kg of the root powder was added into 20 L of 70% ethanol, followed by reflux extraction for 5 hours. The mixture stood for 3 hours to obtain supernatant. The supernatant was filtered and vacuum concentrated to give 214 g of 70% ethanol extract.

<1-4> Preparation of Hexane Extract

Roots of *Lithospermum erythrorhizon* Sieb. Et Zucc grown in Korea were purchased from outlet store of, Jekidong, Seoul in 2003, which were then verified by Department of Herbal Pharmacology, Graduate School of East-West Medical Science, Kyung Hee University. The root samples were dried and pulverized. 3 kg of the root powder was added into 12 L of hexane, followed by extraction at room temperature for 10 days. This extraction was repeated four times and every filtrates obtained from each extraction were vacuum concentrated at under 40° C. The $5^{th}$ and $6^{th}$ extraction were further performed by shaking extraction at room temperature after adding 6 L of a solvent to the remaining sample. After filtering, the extract was vacuum concentrated to give 26 g of hexane extract.

EXAMPLE 2

Separation and Purification of Acetylshikonin

The hexane extract (26 g) obtained in Example <1-4> proceeded onto silica gel column chromatography using open silica gel column (5×40 cm) filled with 1.6 kg of silica gel (FIG. 1). As an extraction solvent, the mixed solvent of hexane and ethylacetate (Hexane:EtOAc=30:1→→1:11) and the mixed solvent of ethylacetate and methanol (EtOAc: MeOH=25:1→→1:2) were used stepwise with increasing polarity. The volume of the mixed solvent was regulated according to the composition of the solvent from 10 l to 4 l and total 421 fractions were obtained by fractioning at every 500 ml unit. Each fraction was investigated its identity by qualitative analysis using HPLC at 520 nm. Fractions with similar patterns were mixed again and re-concentrated to give 30 final concentrated fractions (Fr. 1-30). To examine the homology of those fractions, qualitative analysis was performed using HPLC at 520 nm. Among 30 final fractions, acetylshikonin represented by the following formula 1 and having properties as shown below was separated and purified (1.1 g) from Fr. 6 and Fr. 7. This compound was identified by comparing its NMR data with the already-set up data (S. Y. Hwang, et al., Kor. J. Pharmacogn. 31(3) pp 295-299, 2000, H. W. Cheng, et al., Int. J. Pharm. 120 pp137-144, 1995).

Qualitative analysis was performed with HPLC to confirm the identity of fractions obtained from column chromatography at 520 nm of UV detector. P4000 pump (TSP) and AS1000 autosampler were used as a HPLC system, and Spectra focus UV detector (TSP) was used as a UV detector. YMC-Pack ODS-AM (150×4.6 mm, 4 μm) (YMC, Japan) was used as a HPLC column, and moving phase solvents were all HPLC grade.

TABLE 1

Formula 1

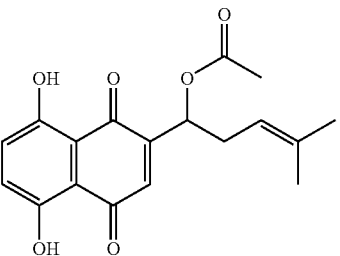

| Carbon | δ C | δ H(j in Hz) |
|---|---|---|
| 1 | 176.68 | — |
| 2 | 148.19 | — |
| 3 | 131.44 | 7.05 s |
| 4 | 178.19 | — |
| 5 | 167.45 | — |
| 6* | 132.85 | 7.24 s |
| 7* | 132.69 | 7.24 s |
| 8 | 166.92 | — |
| 9* | 111.80 | — |
| 10* | 111.54 | — |
| 11 | 69.50 | 6.08 m |
| 12 | 32.81 | 2.66 m (Ha), 2.53 m (Hb) |
| 13 | 117.65 | — |
| 14 | 136.09 | 5.18 m |

TABLE 1-continued

Formula 1

| Carbon | δ C | δ H(j in Hz) |
|---|---|---|
| 15 | 17.92 | 1.64 s |
| 16 | 25.74 | 1.75 s |
| 17 | 169.74 | — |
| 18 | 20.95 | 2.20 s |

EXPERIMENTAL EXAMPLE 1

Defensive Effect of Acetylshikonin in Rats with Local Brain Ischemia Induced by Middle Cerebral Arterial Occlusion <1-1> Preparation of Test Animals Sprague-dawley male rats at 8 weeks having the weight of 280 g-300 g were purchased from Samtako, Inc., Korea. The rats were supplied with feed and water enough and adapted to the experimental environment for one week.

<1-2> Defensive Effect of Acetylshikonin in Rats with Local Brain Ischemia Induced by Middle Cerebral Arterial Occlusion Middle cerebral arterial occlusion was performed by intraluminal suture method based on the method of Zea longa, et al (Zea longa, et al., Stroke, 20, pp 84-91, 1989).

Once middle cerebral artery of a rat is closed, blood flow is interrupted around middle cerebral arterial region so that oxygen and other energy source are exhausted, leading to cell death. In particular, tissue necrosis is observed in the center of the middle cerebral arterial region, striatum and temporal lobe, which is so called 'ischemic core'. Although not middle cerebral arterial region, the neighboring cells begin to be auto-destroyed, which is called 'lischemic penumbra'. 3 hours after blocking middle cerebral artery, necrosis starts and from 6 hours after blocking, cerebral ischemia is developed. The progress of cerebral ischemia continues for 24 hours after middle cerebral artery was closed for 120 minutes, and on the $3^{rd}$ day, it reaches the highest degree. To measure the level of cerebral ischemia, it is necessary to measure correlated infarct volume ($mm^3$). Specifically, subtracting infarct volume ($mm^3$) from contralateral hemisphere makes the volume of cerebral ischemia.

25 mm 4-0 nylon suture was prepared and the end was coated with silicon approximately 5-8 mm long from the very end and diameter was adjusted to 0.30 mm. Rats were anesthetized with 5% isoflurane and a mixed gas of 70% $N_2O$ and 30% $O_2$. A syringe for taking blood sample was inserted in one side and a probe for measuring blood pressure was inserted in the other side. Blood sugar and blood gas were measured from the blood sample. The center of the front neck was open and the right carotid artery and external carotid artery (ECA) were separated carefully. Superior parathyroid gland artery and laryngeal artery, branches of external carotid artery, were cauterized by an electrocautery. Pterygoid palatine artery, a branch of internal carotid artery, was also electriccauterized. External carotid artery was cut and the probe was inserted from external carotid artery to internal carotid artery 18-20 mm away from the common carotid artery and then tied with a thread. The opened skin was stitched and the rat was recovered from the anesthesia.

Right after and 120 minutes after brain ischemia was induced, the water extract of *Lithospermum erythrorhizon* Sieb. Et Zucc (300 mg/kg), the alcohol extract of *Lithospermum erythrorhizon* Sieb. Et Zucc (300 mg/kg) the 70% alcohol extract of *Lithospermum erythrorhizon* Sieb. Et Zucc (300 mg/kg) and acetylshikonin (1 mg/kg and 3 mg/kg) were orally administered. To investigate dose dependent effect of those samples, 100 and 300 mg/kg of the samples were diluted in triple distilled water and orally administered by 3 ml per±0.5 g of weight of the rat. The numbers of rats with brain ischemia induced were equal in every experimental group and the induction was performed on the same day. Operation was performed at the body temperature of 37±0.5° C. 120 minutes after the operation, rats were re-anesthetized and the probe was backed for reperfusion. 22 hours after the reperfusion, cervical dislocation was carried out. Within two minutes from the cervical dislocation, the brain was extracted and 7 sections with 2 mm thickness were prepared. The sections were dipped in a 16 well plate containing 2% triphenyltetrazolium chloride (TTC), which stood at 37° C. for 30 minutes. Then, the sections were fixed in 4% paraformaldehyde, and the tissues were observed. Operations were performed under operating microscope. Lamp light was used not to reduce body temperature under 37° C. Each tissue was photographed by a digital camera, which was inputted in computer. Optimas 6.5 (Bioscan), an image analysis program, was used to calculate the volume of damaged tissues (%) and the level of cerebral ischemia (%) caused by the induction of cerebral ischemia by the following mathematical formula 1 and mathematical formula 2.

Correlated Infarct Volume (a)=(volume of normal hemisphere)−(volume of normal area of damaged hemisphere)                    <Mathematical Formula 1>

Infarct Rate (%)=((volume of normal hemisphere ($mm^3$)−correlated infarct volume ($mm^3$))/volume of normal hemisphere ($mm^3$))×100     <Mathematical Formula 2>

Figure 2:
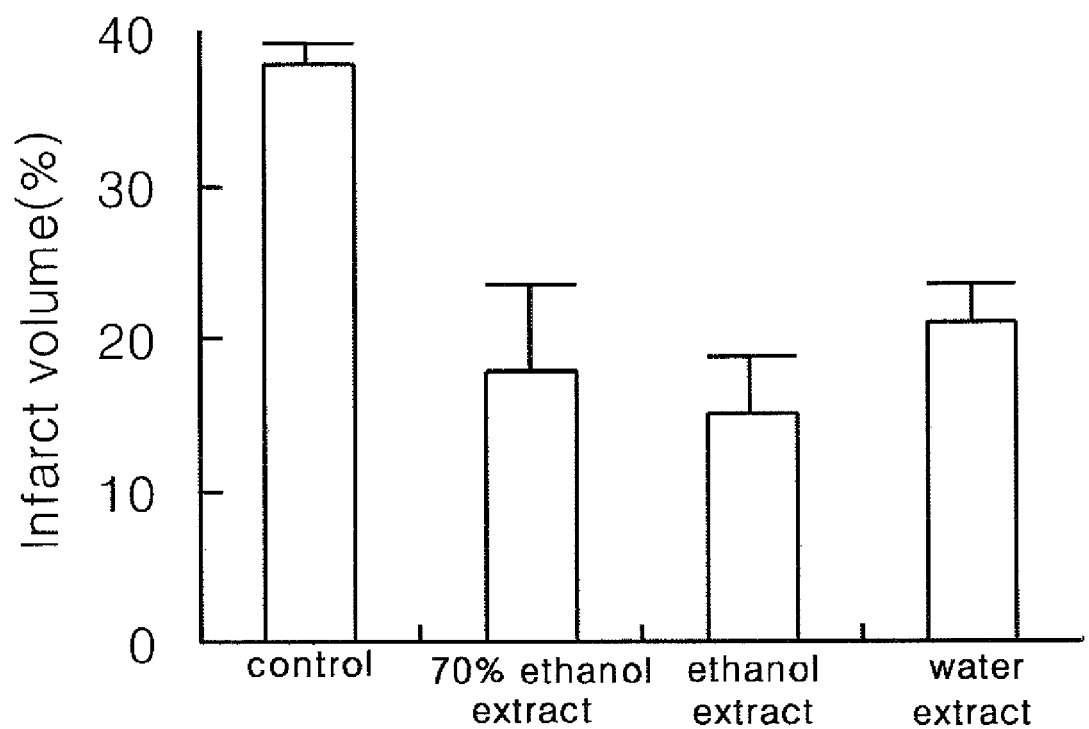
FIG. 2 is a graph illustrating the defensive action of the extract of Lithospermum erythrorhizon Sieb. Et Zucc of the invention in a rat with local brain ischemia by MCAo, which was compared with the control group.
Figure 3:
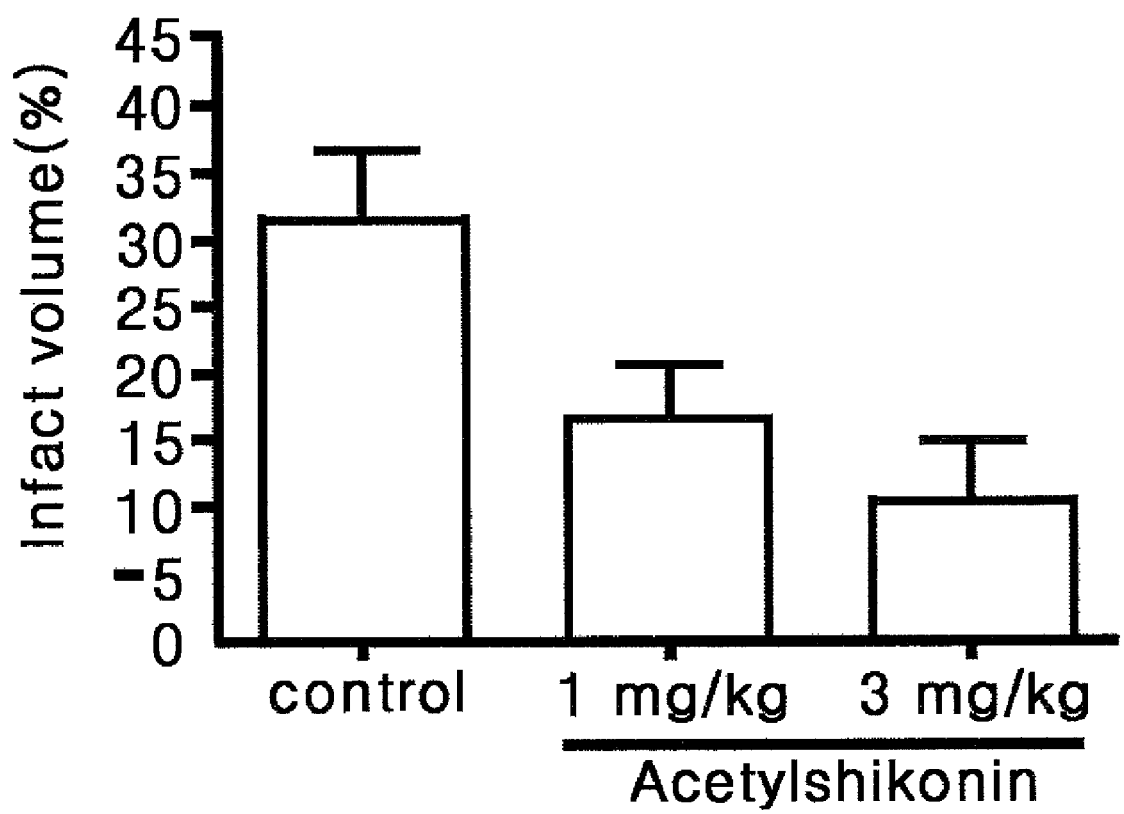
FIG. 3 is a graph illustrating the defensive action of acetylshikonin of the invention in a rat with local brain ischemia by MCAo, which was compared with the control group.

As a result, the administration of the water extract (300 mg/kg), the alcohol extract (300 mg/kg), and the 70% alcohol extract (300 mg/kg) of *Lithospermum erythrorhizon* Sieb. Et Zucc exhibited protective effect on brain tissue damage respectively by 44.73%, 60.72% and 52.63%, compared with the control (FIG. 2). As shown in FIG. 2, acetylshikonin administration also brought the protective effect on brain tissue damage dose-dependently: 1 mg/kg of acetylshikonin exhibited 46.88% protective effect and 3 mg/kg of acetylshikonin exhibited 68.75% protective effect, compared with the control (FIG. 3). For the statistical interpretation, each result was compared between experimental group and control group and analyzed by One-way ANOVA (Prism4, GraphicPad software) (*$p<0.05$, $p<0.01$, *$p<0.001$).

EXPERIMENTAL EXAMPLE 2

Inhibitory Effect of Acetylshikonin on NO Generation

<2-1> Inhibition of NO Generation by Acetylshikonin in BV-2 Cells and Microglia Cells Activated by LPS To investigate the effect of acetylshikonin on the activation of microglia cells which are macrophages in brain, NO generation was measured in BV-2 cells and primary microglia cells which are neuroglia cells, activated by lipopolysaccharide according to the previously reported methods with slight modifications (Min Kim J, et al., Neuroreport, 14(15), pp1941-1944, 2003).

BV-2 cells (Lab. of Dr. Eui-Ju Choi, Korea University) were maintained in DMEM (Dulbeccols Modified Eagle Medium, Gibco-BRL, England) supplemented with 10% FBS (Fetal Bovine Serum, Gibco-BRL, England) and 1% penicillin-streptomycin (Gibco-BRL, England). To obtain the primary microglia cells, brain cells were separated from the brain extracted from Sprague-Dawley rat (Taconic, Japan) at less than 1 week from the birth and the cells were cultured for approximately 2 weeks in DMEM having the same composition with the one used for BV-2 cell culture in a 75T flask and then the primary microglia cells were recovered. BV-2 cells and the primary microglia cells were distributed into a 96 well plate at the concentration of $4\times10^{-4}$ cells/well and then cultured in a 37° C., 5% $CO_2$ incubator for overnight. Acetylshikonin of the present invention in DMSO (dimetyl sulfoxide, Sigma, USA) was treated to BV-2 and the primary microglia cells (0.1, 0.5, and 1 uM), to which 100 ng/ml of lipopolysaccaride was treated to activate the cells. 0.5 mM of NGMMA (N super(G)-monomethyl-L-arginine, Sigma, USA), a NOS inhibitor, was treated together with 100 ng/ml of lipopolysaccaride as a positive control. 24 hours later, 50 μl of each BV-2 cell and microglia cell culture medium was obtained and mixed with 50 μl of Griess reagent, which stood at room temperature for 10 minutes. $OD_{570}$ was measured by Elyzerleader (Moleulat Device, USA) and the concentration was calculated by considering the level of sodium nitrite as standard.

Figure 4:
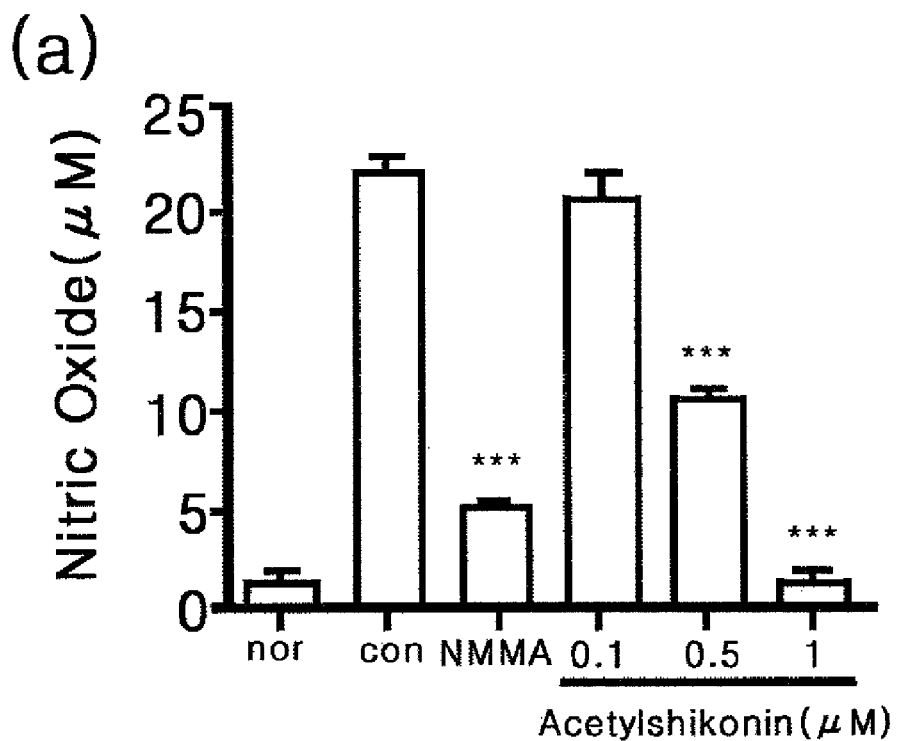
FIG. 4a is a graph illustrating the generation of nitric oxide (NO) when acetylshikonin was treated to BV-2 cells activated by lipopolysaccharide (LPS)
FIG. 4b is a graph illustrating the generation of NO when acetylshikonin was treated to primary microglia cells activated by LPS.
Figure 4:
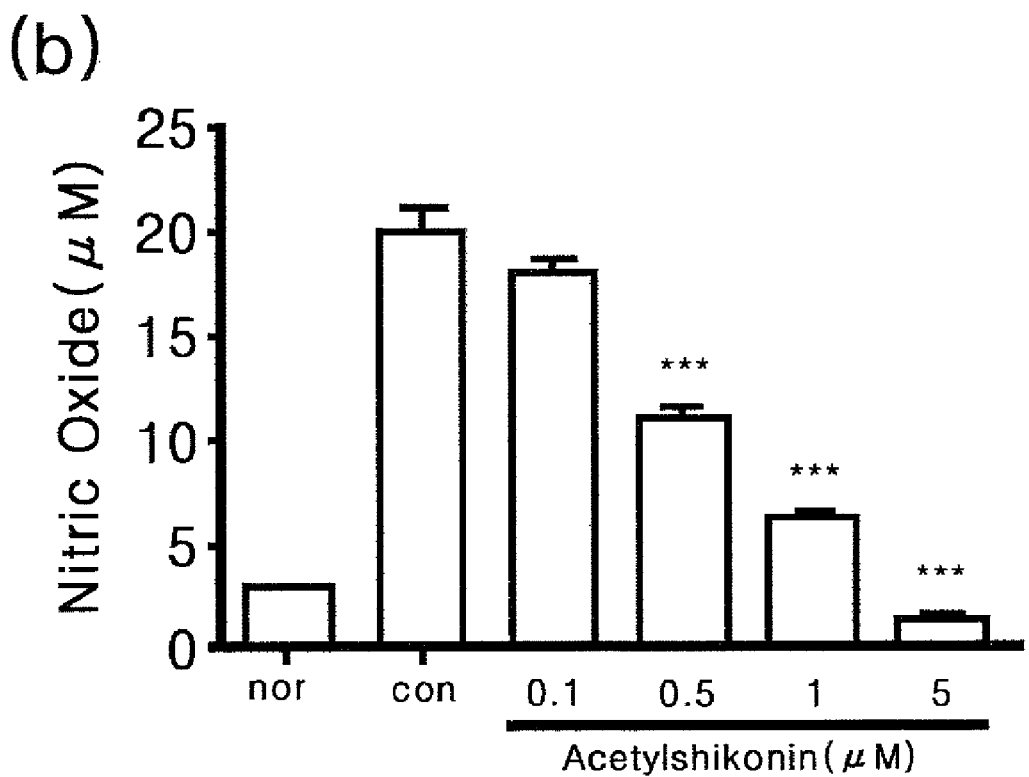

As a result, as shown in FIGS. 4a and 4b, inhibition of NO generation by acetylshikonin was observed in both groups treated with 1 uM of acetylshikonin and the positive control group.

EXPERIMENTAL EXAMPLE 3

Inhibition of iNOS Expression by Acetylshikonin

<3-1> Inhibition of iNOS mRNA Expression by Acetylshikonin

To investigate the inhibition of iNOS mRNA expression by acetylshikonin, KT-PCR was performed.

The primary microglia cells cultured in DMEM supplemented with 10% FBS and 1% penicillin-streptomycin were distributed in a 6 well plate at the concentration of $4\times10^6$ cells/well, followed by culture for 24 hours. 100 ng/ml of lipopolysaccharide and 0.1, 1 uM of acetylshikonin were co-treated thereto, followed by activation of the cells for 24 hours. The control group was not treated with lipopolysaccaride. After 24 hours of activation, the culture medium was discarded and the cells were washed with cold PBS (phosphate Base Solution), to which trypsin was treated. 1 ml of PBS containing the cells was obtained, followed by centrifugation at 12,000 rpm for 2 minutes to separate the cells. The cells were lysed in RNA separation solution (easyblue) to extract RNA from the cells, followed by centrifugation at 12,000 rpm for 15 minutes. After treating chloroform, centrifugation was performed again at 13,000 rpm for 25 minutes and the supernatant was obtained and washed with isopropanol to extract RNA. cDNA was synthesized using 5 ug of the RNA and 5 μmol of primer at 45° C., followed by PCR. PCR was performed as follows; predenaturation at 95° C. for 5 minutes, denaturation at 94° C. for 50 seconds, annealing at 50° C. for 1 minute, polymerization at 72° C. for 1 minute, 32 cycles from denaturation to polymerization, and final extension at 72° C. for 5 minutes. The PCR product was transferred on to 1.5% agarose gel stained with etidium bromide for electrophoresis.

Figure 5:
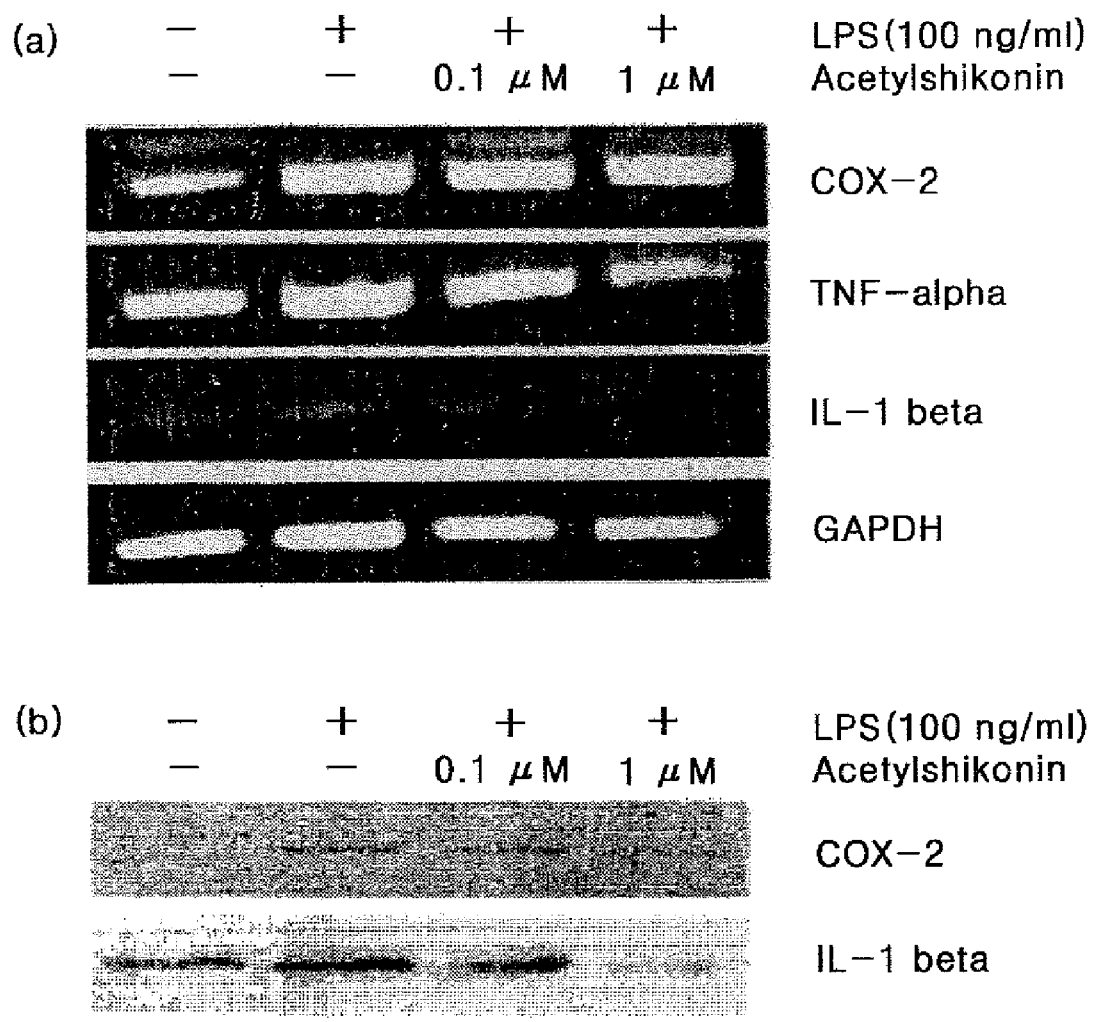
FIG. 5a is a set of photographs illustrating the result of reverse transcription-polymerase chain reaction (RT-PCR) exhibiting the inhibiting effects of acetylshikonin on the expressions of messenger RNAs (mRNA) of inducible nitric oxide synthase (iNOS), interleukin-1beta (IL-1beta) and tumor necrosis factor-alpha(TNF-alpha) in primary microglia cells activated by lipopolysaccharide.
FIG. 5b is a set of photographs illustrating the result of Western blot analysis exhibiting the inhibiting effects of acetylshikonin on the expressions of iNOS and IL-1 beta in primary microglia cells activated by lipopolysaccharide.

As a result, as shown in FIG. 5a, it was confirmed that acetylshikonin inhibited the expression of mRNAs of iNOS, IL-1beta and TNF-alpha in the primary microglia cells significantly and dose-dependently.

<3-2> Inhibition of iNOS Expression by Acetylshikonin

Western blot analysis was performed to investigate the inhibition of iNOS expression by acetylshikonin.

The primary microglia cells cultured in DMEM supplemented with 10% FBS and 1% penicillin-streptomycin were distributed in a 6 well plate at the concentration of $4 \times 10^6$ cells/well, followed by culture for 24 hours. 100 ng/ml of lipopolysaccharide and 0.1, 1 uM of acetylshikonin were co-treated thereto, followed by activation of the cells for 24 hours. The control group was not treated with lipopolysaccharide. After 24 hours of activation, the culture medium was discarded and the cells were washed with cold PBS, to which trypsin was treated. 1 ml of PBS containing the cells was obtained, followed by centrifugation at 12,000 rpm for 2 minutes to separate the cells. The cells were loaded in 50 μl of triple lysis buffer to decompose all the cell membranes and then centrifugation was performed at 12,000 rpm for 30 minutes to obtain supernatant, a protein layer. The obtained supernatant was diluted and protein was quantified by Bradford method. After quantification, an equal amount of protein proceeded onto 8% polyacrylamide gel electrophoresis. The separated proteins from the electrophoresis were transferred onto Hybond ECL nitrocellulose membrane, leading to the reaction with primary and secondary antibodies of iNOS and IL-1beta. ECL examination was performed.

As a result, as shown in FIG. 5b, it was confirmed that acetylshikonin inhibited the expressions of iNOS and IL-1beta, inflammatory cytokines, in the primary microglia cells significantly and dose-dependently.

EXPERIMENTAL EXAMPLE 4

Acute Toxicity Test

<4-1> Oral Administration

ICR mice and Sprague-dawley rats were grouped by 10 per group, 8 groups for each, which were oral-administered respectively with 100, 250, 500 and 1000 mg/kg of the extract and compound of the present invention. Toxicity was observed for 2 weeks. No death was observed and no specific symptoms were found in those experimental groups, compared with the control group.

<4-2> Intraperitoneal Administration

ICR mice (25±5 g) and Sprague-dawley rats were grouped by 10 per group, 8 groups for each, which were intraperitoneal-administered respectively with 25, 50, 100 and 200 mg/kg of the extract and compound of the present invention. Toxicity was observed for 24 hours. No death was observed and no specific symptoms were found in those experimental groups, compared with the control group.

As a result, the compound of the present invention was confirmed to be safe with nearly no acute toxicity.

Manufacturing Examples of the pharmaceutical composition containing the compound of the invention are described hereinafter, but these examples are given to explain the invention in more detail and cannot limit the present invention thereto.

MANUFACTURING EXAMPLE 1

Preparation of Powders

<1-1> Preparation of Powders Containing the Extract

| | |
|---|---|
| Water extract of *Lithospermum erythrorhizon* Sieb. Et Zucc | 300 mg |
| Lactose | 50 mg |
| Talc | 10 mg |

Powders were prepared by mixing all the above components and filled airtight bags with them.

<1-2> Preparation of Powders Containing Acetylshikonin

| | |
|---|---|
| Acetylshikonin | 20 mg |
| Lactose | 100 mg |
| Talc | 10 mg |

Powders were prepared by mixing all the above components and filled airtight bags with them.

MANUFACTURING EXAMPLE 2

Preparation of Tablets

<2-1> Preparation of Tablets Containing the Extract

| | |
|---|---|
| Ethanol extract of *Lithospermum erythrorhizon* Sieb. Et Zucc | 300 mg |
| Corn starch | 50 mg |
| Lactose | 50 mg |
| Magnesium stearate | 2 mg |

Tablets were prepared by mixing all the above components by the conventional method for preparing tablets.

<2-2> Preparation of Tablets Containing Acetylshikonin

| | |
|---|---|
| Acetylshikonin | 10 mg |
| Corn starch | 100 mg |
| Lactose | 100 mg |
| Magnesium stearate | 2 mg |

Tablets were prepared by mixing all the above components by the conventional method for preparing tablets.

MANUFACTURING EXAMPLE 3

Preparation of Capsules

<3-1> Preparation of Capsules Containing the Extract

| | |
|---|---|
| Water extract of *Lithospermum erythrorhizon* Sieb. Et Zucc | 300 mg |
| Crystalline cellulose | 3 mg |
| Lactose | 14.8 mg |
| Magnesium stearate | 0.2 mg |

Capsules were prepared by mixing the components above and filled gelatin capsules with the mixture according to the conventional method for preparing capsules.

<3-2> Preparation of Capsules Containing Acetylshikonin

| Acetylshikonin | 10 mg |
|---|---|
| Crystalline cellulose | 3 mg |
| Lactose | 14.8 mg |
| Magnesium stearate | 0.2 mg |

Capsules were prepared by mixing the components above and filled gelatin capsules with the mixture according to the conventional method for preparing capsules.

MANUFACTURING EXAMPLE 4

Preparation of Injectable solutions

| Acetylshikonin | 10 mg |
|---|---|
| Mannitol | 180 mg |
| Sterilized distilled water | 2974 mg |
| $Na_2HPO_4 \cdot 12H_2O$ | 26 mg |

Injectable solutions containing the above components by the above composition (2 ml/ampoule) were prepared by the conventional method for preparing injectable solutions.

MANUFACTURING EXAMPLE 5

Preparation of Liquid Formulations

<5-1> Preparation of Liquid Formulations Containing the Extract

| 70% ethanol extract of *Lithospermum erythrorhizon* Sieb. Et Zucc | 200 mg |
|---|---|
| Isomerized sugar | 10 g |
| Mannitol | 5 g |
| Refined water | proper amount |

Each component was dissolved in refined water according to the conventional production method for liquid formulation, to which lemon flavor was added. Refined water was added to the above components to make the total volume to 100 ml. The above components were mixed, filled in a brown bottle and sterilized to prepare liquid formulations.

<5-2> Preparation of Liquid Formulations Containing Acetylshikonin

| Acetylshikonin | 20 mg |
|---|---|
| Isomerized sugar | 10 g |
| Mannitol | 5 g |
| Refined water | proper amount |

Each component was dissolved in refined water according to the conventional production method for liquid formulation, to which lemon flavor was added. Refined water was added to the above components to make the total volume to 100 ml. The above components were mixed, filled in a brown bottle and sterilized to prepare liquid formulations.

MANUFACTURING EXAMPLE 6

Preparation of Health Beverages

<6-1> Preparation of Health Beverages Containing the Extract

| Water extract of *Lithospermum erythrorhizon* Sieb. Et Zucc | 1000 mg |
|---|---|
| Vitamin C | 15 g |
| Vitamin E (powder) | 100 g |
| Ferrous lactate | 19.75 g |
| Zink oxide | 3.5 g |
| Nicotinic acid amide | 3.5 g |
| Vitamin A | 0.2 g |
| Vitamin B1 | 0.25 g |
| Vitamin B2 | 0.3 g |
| Water | proper amount |

<6-2> Preparation of Health Beverages Containing Acetylshikonin

| Acetylshikonin | 200 mg |
|---|---|
| Vitamin C | 15 g |
| Vitamin E (powder) | 100 g |
| Ferrous lactate | 19.75 g |
| Zink oxide | 3.5 g |
| Nicotinic acid amide | 3.5 g |
| Vitamin A | 0.2 g |
| Vitamin B1 | 0.25 g |
| Vitamin B2 | 0.3 g |
| Water | proper amount |

The above components were mixed according to the conventional health beverage production method, and the mixture was heated with stirring at 85° C. for one hour. The solution was filtered and stored in a sterilized 2 l container with sealed and sterilized. The container was then stored in a refrigerator for further use as a health beverage composition.

The composition of the beverage followed the preferable combination of each component but not always limited thereto and can be modified considering demand class, demand country, purpose of use, local and national preference, etc.

What is claimed is:

1. A method for protecting neurons from reperfusion injury, comprising administering to a mammal having brain ischemia or having suffered brain ischemia, an effective dose of a pharmaceutical composition containing an extract of *Lithospermum erythrorhizon* Sieb Et Zucc roots or acetylshikonin, whereby said acetylshikonin is represented by the following formula:

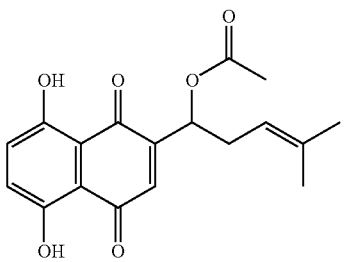

and wherein the extract of *Lithospermum erythrohizon* Sieb Et Zucc is prepared by extracting *Lithospermum erythrorhizon* Sieb Et Zucc roots with water, alcohol or a mixture thereof.

2. The method according to claim 1, wherein the acetylshikonin is isolated by a process comprising extracting a water extract, alcohol extract or aqueous,alcoholic extract of *Lithospermum erythrorhizon* Sieb Et Zucc roots with a fat-soluble solvent or by extracting *Lithospermum erythrorhizon* Sieb Et Zucc roots with a fat-soluble solvent.

3. The method according to claim 2, wherein the fat-soluble solvent is selected from the group consisting of n-butanol, hexane, ethylacetate and chloroform.

4. The method of claim 1, wherein said pharmaceutical composition contains acetylshikonin represented by the following formula:

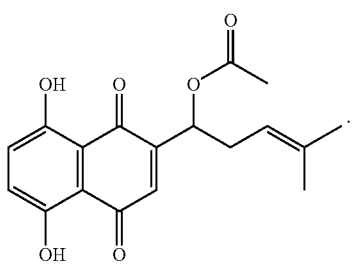

5. The method of claim 1, wherein said protecting includes inhibition of neuronal apoptosis caused by reperfusion due to brain ischemia.

* * * * *